(12) United States Patent  
Gordaninejad et al.

(10) Patent No.: US 7,698,930 B2  
(45) Date of Patent: Apr. 20, 2010

(54) METHOD AND APPARATUS FOR MEASURING PRESSURE DROP OF MAGNETO-RHEOLOGICAL SUSPENSIONS IN MICROCHANNELS

(75) Inventors: Faramarz Gordaninejad, Reno, NV (US); Joseph L. Whiteley, Gardnerville, NV (US)

(73) Assignee: Board of Regents of the Nevada System of Higher Education on behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 11/732,700

(22) Filed: Apr. 3, 2007

(65) Prior Publication Data

US 2007/0284202 A1 Dec. 13, 2007

Related U.S. Application Data

(60) Provisional application No. 60/788,897, filed on Apr. 4, 2006.

(51) Int. Cl.  
*G01N 11/08* (2006.01)
(52) U.S. Cl. .................................................. 73/54.09
(58) Field of Classification Search ............ 73/54.01, 73/54.09; 137/807  
See application file for complete search history.

(56) References Cited

U.S. PATENT DOCUMENTS 6,318,970 B1 * 11/2001 Backhouse ................... 417/92  
2004/0266319 A1 * 12/2004 Kordonski et al. ............. 451/5  
2006/0010964 A1 * 1/2006 Sparks et al. .............. 73/54.01

OTHER PUBLICATIONS

Acrivos, et al., "Squeezing Flow of Particles and Large Molecules Suspended in a Liquid Through Nanochannels," *Nanotech* 2002 vol. 1, *Technical Proceedings of the 2002 International Conference on Modeling and Simulation of Microsystems*, 66-67 (2002).

Ahn, et al., "Fluid Micropumps Based on Rotary Magnetic Actuators," *Proceedings of the 1995 IEEE Micro Electro Mechanical Systems Conference*, Jan. 29-Feb. 2, 1995, 408-412 (1995).

Barberi, et al., "Probing the Inner Surface of a Capillary With the Atomic Force Microscope," *Electrophoresis*, 16:1445-1450 (1995).

(Continued)

*Primary Examiner*—Hezron Williams  
*Assistant Examiner*—Mark Shabman  
(74) *Attorney, Agent, or Firm*—UNR-DRI Technology Transfer Office; Ryan A. Heck (57) ABSTRACT

Methods and apparatus are disclosed for characterizing flow of magneto-rheological suspensions through microchannels. The apparatus includes a pump for pumping a the magneto-rheological suspension; a microchannel hydraulically coupled to the pump and configured to receive the magneto-rheological suspension from the pump; a manifold hydraulically coupled between an outlet of the microchannel and the pump; a static pressure tap configured to convey a static pressure of the manifold; a pressure sensor hydraulically coupled to the pressure tap and configured to receive the static pressure conveyed therefrom; and a magnet positioned to direct a magnetic field toward the microchannel and contents disposed therein.

28 Claims, 6 Drawing Sheets

OTHER PUBLICATIONS

Berthier, et al., "Numerical Modeling of Ferrofluid Flow Instabilities in a Capillary Tube at the Vicinity of a Magnet," *NanoTech* 2002 vol. 2, *Technical Proceedings of the 2002 International Conference on Modeling and Simulation of Microsystems*, 40-43 (2002).

Bica, "Plasma Device for Magnetic Nanoparticles Production," *Journal of Magnetism and Magnetic Materials*, 201:45-48 (Jul. 1, 1999).

Bohl, et al., "Development of Stereoscopic Molecular Tagging Velocimetry," *Experiments in Fluids*, 30:302-308 (2001).

Carlson, et al., "Commercial Magneto-Rheological Fluid Devices," *5th Int. Conf. on Electro-Rheological, Magneto-Rheological Suspensions and Associated Technology*, Sheffield, Jul. 10-14, 1995.

Carlson, "What Makes a Good MR Fluid?," *The 8th International Conference on Electrorheological (ER) Fluids and Magnetorheological (MR) Suspensions*, Nice, Jul. 9- 13, 2001.

Chaudhuri, et al., "Rheological Parameter Estimation for a Ferrous Nanoparticle-Based Magnetorheological Fluid Using Genetic Algorithms," *Smart Structures and Materials 2004: Active Materials: Behavior and Mechanics, Proceedings of SPIE*, 5387:503-512 (2004).

Chen, et al., "Gold-coated Iron Nanoparticle for Biomedical Applications," *Journal of Applied Physics*, 93(10):7551-7553 (May 15, 2003).

Choi, et al., "Fluid Flow and Heat Transfer in Microtubes," *Micromechanical Sensors, Actuators, and Systems*, 32:123-134(1991).

Deshmukh et al., "Structure Formation, Dynamics and Applications of MR Fluids in Microchannels," *The Society of Rheology, 77th Annual Meeting* (Oct. 2005), 2 pages http://www.rheology.org/SoR05a/abstract.asp?PaperID=258, printed May 21, 2007, *abstract only*.

Dimock, et al., "Bingham Biplastic Analysis of Shear Thinning and Thickening in Magnetorheological Dampers," *Proceedings of SPIE, Smart Structures and Materials 2000: Smart Structures and Integrated Systems*, 3985:444-455 (2000).

Flores et al., "Embolization of Blood Vessels as a Cancer Therapy Using Magnetorheological Fluids," *Journal of Intelligent Material Systems and Structures*, 13(10):641-646, *abstract only* (2002).

Forbes, et al., "An Approach to Targeted Drug Delivery Based on Uniform Magnetic Fields," *IEEE Transactions on Magnetics*, 39(5):3372-3377 (Sep. 2003).

Gad-el-Hak, "Fluid Mechanics of Microdevices—The Freeman Scholar Lecture," *Journal of Fluids Engineering*, 121(1):5-33 (Mar. 1999).

Gans, et al., "Preparation and Magnetisation of a Silica-Magnetite Inverse Ferrofluid," *Journal of Magnetism and Magnetic Materials*, 201:11-13 (1999).

Gans, et al., "The Influence of Particle Size on the Magnetorheological Properties of an Inverse Ferrofluid," *Journal of Chemical Physics*, 113(5):2032-2042 (Aug. 1, 2000).

Gong, et al., "Design, Optimization and Simulation On Microelectromagnetic Pump," *Sensors and Actuators, A: Physical*, 83(1):200-207 (2000).

Greivell, et al., "The Design of a Ferrofluid Magnetic Pipette," *IEEE Transactions on Biomedical Engineering*, 44(3):129-135 (Mar. 1997).

Haghgooie, "Dynamics of Biopolymers and Complex Fluids," 2 pages http://web.mit.edu/doylegroup/raminbio.html (printed Jan. 30, 2009).

Hatch, et al., "A Ferrofluidic Magnetic Micropump," *Journal of Microelectromechanical Systems*, 10(2):215-221 (Jun. 2001).

Ho, et al., "A Feasibility Study of Magneto-Rheological Fluids in MEMS Devices," *Proceedings of the 1998 Symposium on Image, Speech, Signal Processing, and Robotics*, I:347-350 (Sep. 1998).

Jang, et al., , "Theoretical and Experimental Study of MHD (magnetohydrodynamic) micropump," *Sensors and Actuators, A: Physical*, 80(1):84-89 (2000).

Jansen, et al., "Semi-Active Control Strategies for MR Dampers: A Comparative Study," *Journal of Engineering Mechanics*, 126(8):795-803 (2000).

Jensen, et al., "The Clogging Pressure of Bubbles in Hydrophilic Microchannel Contractions," *Journal of Micromechanics and Microengineering*, 14:876-883 (2004).

Judy, et al., "Characterization of Frictional Pressure Drop for Liquid Flows Through Microchannels," *International Journal of Heat and Mass Transfer* 45:3477-3489 (2002).

Kamath, et al., "Analysis and Testing of Bingham Plastic Behavior in Semi-Active Electrorheological Fluid Dampers," *Smart Materials and Structures*, 5(5):576-590 (Oct. 1996).

Kaupp, et al., "Characterization of Inner Surface and Adsorption Phenomena in Fused-Silica Capillary Electrophoresis Capillaries," *Journal of Chromatography A*, 744:93-101 (1996).

Kaupp, et al., "Characterization of Inner Surface Phenomena in Capillary Electrophoresis Capillaries by Electron Microscopy, Atomic Force Microscopy and Secondary Ion Mass Spectroscopy," *Journal of Chromatography A*, 781:55-65 (1997).

Kim, et al., "Biomedical Application of Ferrofluids Containing Magnetite Nanoparticles," *Mat. Res. Soc. Symp. Proc.* 676 (2001).

Klein et al., "High Winding Density Micro Coils for Magnetic Actuators" *Microsystem Technologies*, 4:172-75 (1998).

Kohl, "Fluidic Actuation by Electrorheological Microdevices," *Mechatronics*, 10(4-5):583-594 (Jun. 2000).

Koo, et al., "Liquid Flow in Microchannels: Experimental Observations and Computational Analyses of Microfluidics Effects," *Journal Micromechanics and Microengineering*, 13:568-579 (May 14, 2003).

Kormann et al., "MR Fluids with Nano-Sized Magnetic Particles," *International Journal of Modern Physics B*, 10:3167-72 (1996).

Kuzhir, et al., "Effect of the Orientation of the Magnetic Field on the Flow of Magnetorheological Fluid. II. Cylindrical Channel," *Journal of Rheology*, 47(6):1385-1398 (Nov./Dec. 2003).

Lauger, et al., "Magneto Sweep—A New Method for Characterizing the Viscoelastic Properties of Magneto-Rheological Fluids," *Journal of Applied Rheology*, 25-31 (Jan./Feb. 2002).

Lee, et al., "Application of Metallic Nanoparticle Suspensions in Advanced Cooling Systems," *Recent Advances in Solids/Structures and Application of Metallic Materials*, PVP-vol. 342/MD-vol. 72:227-234 (Nov. 1996).

Lee, et al., "Characteristics of an Electro-Rheological Fluid Valve Used in an Inkjet Printhead," *Smart Materials and Structures* 9:839-847 (2000).

Lee, et al., "Experimental Study on Electro-Rheological Material With Grooved Electrode Surfaces," *Materials and Design*, 22(4):277-283 (Jun. 2001).

Lemoff, et al., "An AC Magnetohydrodynamic Micropump," *Sensors and Actuators, B: Chemical*, 63(3):178-185 (2000).

Lim, et al., "Magnetorheology of Carbonyl-Iron Suspensions With Submicron-Sized Filler," *IEEE Transactions on Magnetics*, 40(4):3033-3035 (Jul. 2004).

Liu et al., "In-vitro Investigation of Blood Embolization in Cancer Treatment Using Magnetorheological Fluids," *Journal of Magnetism and Magnetic Materials*, 225:209-17 (2001).

Ly, et al., "Simulations of Particle Dynamics in Magnetorheological Fluids," *Journal of Computational Physics*, 155:160-177 (1999).

Melle, et al., "Structure and Dynamics of Magnetorheological Fluids in Rotating Magnetic Fields," *Physical Review E*, 61(4):4111-4117 (Apr. 2000).

Mala, et al., "Flow Characteristics of Water in Microtubes," *International Journal of Heat and Fluid Flow*, 20(2):142-148 (Apr. 1999).

Nishiyama, et al., "Damping Characteristics of MR Fluids in Low Magnetic Fields," *International Journal of Modern Physics B*, 15(6 & 7):829-836 (2001).

Pang, et al., "Analysis and Testing of a Linear Stroke Magnetorheological Damper," *Proceedings of the 1998 39th AIAA/ASME/ASCE/AHS/ASC Structures, Structural Dynamics, and Materials Conference and Exhibit and AIAA/ASME/AHS Adaptive Structures Forum*, Apr. 20-23, 1998, Long Beach, CA, CP9803(4):2841-2856 (1998).

Papautsky, et al., "Microchannel Fluid Behavior Using Micropolar Fluid Theory," *Proceedings of the 1998 IEEE 11th Annual International Workshop on Micro Electro Mechanical Systems*, Jan. 25-29, 1998, 544-549 (1998).

Papautsky, et al., "Effects of Rectangular Microchannel Aspect Ratio On Laminar Friction Constant," *SPIE Proceedings: Microfluidic Devices and Systems II*, 3877:322 pages (1999).

Papautsky, et al., A Review of Laminar Single-Phase Flow in Microchannels, *Proceedings of 2001 ASME International Mechanical Engineering Congress and Exposition*, Nov. 11-16, 2001, New York, NY (2001).

Park, et al., "Design of Magnetic Fluid Linear Pump," *IEEE Transactions on Magnetics* 35(5):4058-4060 (Sep. 1999).

Park, et al., "Micro Fluid Control System Using Homogeneous ER Fluids," *1999 IEEE/RSJ International Conference on Intelligent Robots and Systems (IROS'99): Human and Environment Friendly Robots with High Intelligence and Emotional Quotients'*, Oct. 17-Oct. 21, 1999, 2:1063-1068 (1999).

Park, et al., "New Structure of the Magnetic Fluid Linear Pump," *IEEE Transactions on Magnetics*, 36(5):3709-3711 (Sep. 2000).

Park, et al., "Electrorheology and Magnetorheology," *Korea-Australia Rheology Journal*, 13(1):13-17 (Mar. 2001).

Perez-Castillejos, et al., "The Use of Ferrofluids in Micromechanics," *Sensors and Actuators, A: Physical*, 84(1):176-180 (Aug. 2000).

Pfund, et al., "Pressure Drop Measurements in a Microchannel," *AIChe Journal*, 46(8):1496-1507 (Aug. 2000).

Phan-Thien, et al., "Dissipative Particle Dynamics Modelling of Complex-Structured Fluids in Microchannel Flows," *Division of Bioengineering HPCES Singapore MIT Alliance at the National University of Singapore, and the Singapore Institute of High Performance Computing*.

Pullen, et al., "Characterization by Atomic Force Microscopy of Fused-Silica Capillaries Chemically Modified for Capillary Electrokinetic Chromatography," *Analytical Chemistry*, 72(13):2751-2757 (Jul. 1, 2000).

Rong, et al., "Flexible Fixturing with Phase-Change Materials. Part 1. Experimental Study on Magnetorheological Fluids," *International Journal of Advanced Manufacturing Technology*, 16(11):822-829 (2000).

Sharp, "Experimental Investigation of Liquid and Particle-Laden Flows in Microtubes," *PhD Thesis, University of Illinois at Urbana-Champaign*, 267 pages (2001).

Sharp, et al., "Shear-Induced Arching of Particle-Laden Flows in Microtubes," *Proceedings of 2001 ASME International Mechanical Engineering Congress and Exposition*, Nov. 11-16, 2001.

Sharp, et al., "Transition from Laminar to Turbulent Flow in Liquid Filled Microtubes," *Experiments in Fluids*, 36(5):741-747 (May 2004).

Sims, et al., "Electrorheological long-stroke damper: a new modelling technique with experimental validation," *Journal of Sound and Vibration*, 229(2):207-227 (2000).

Snyder, et al., "Characterization of a magnetorheological fluid damper using a quasi-steady model," *Proceedings of SPIE*, 3668:507-519 (1999).

Stanci, et al., "Magnetofluidic Sensor for Volume Measurement," *Sensors and Actuators*, 84:246-249 (2000).

Timco, et al., "Magnetorheological Properties of some Ferrofluids," *IEEE Transactions on Magnetics*, 30(2):1117-1119 (Mar. 1994).

Trihan, et al., "Impact of Varying Concentrations of Nanometer Sized Particles in a Bidisperse Magnetorheological Fluid," *Smart Structures and Materials 2003: Damping and Isolation, Proceedings of SPIE*, 5052:175-185 (2003).

Voit, et al., "Magnetic Behavior of Coated Superparamagnetic Iron Oxide Nanoparticles in Ferrofluids," *Mat. Res. Soc. Symp. Proc.*, 676:Y7.8.1-Y7.8.6 (2001).

Wagener, et al., "Sputtering On Liquids—a Versatile Process for the Production of Magnetic Suspensions?," *Journal of Magnetism and Magnetic Materials*, 201:41-44 (Jul. 1, 1999).

Wang et al., "Flow Analysis of Field-Controllable, Electro- and Magneto-Rheological Fluids Using Herschel-Bulkley Model," *J. Intelligent Matls., Systems and Structures*, 10(8):601-08 (Aug. 1999).

Xu, et al., "Study on the Viscosity of the Liquid Flowing in Microgeometry," *J. Micromech. Microeng.*, 9:377-384 (1999).

Yalcintas, et al., "Magnetorheological and Electrorheological Materials in Adaptive Structures and Their Performance Comparison," *Smart Materials and Structures*, 8(5):560-573 (1999).

Yamaguchi, et al., "Theoretical and Experimental Study of Microchannel Blockage Phenomena," *XXI ICTAM*, Aug. 15-21, 2004, Warsaw, Poland.

Yokota, et al., "A Pressure Control Valve Using MR Fluid," *Nihon Kikai Gakkai Kanto Shibu. Seimitsu Kogakkai Yamanashi Koenkai Koen Ronbunshu*, 133-134 (1999).

Yokota, "Micro Actuators Using Functional Fluids," *The Fourth International Symposium on Fluid Power Transmission and Control*, Apr. 8-10, 2003.

Yoshida, et al., "In-Pipe Mobile Micromachine Using Fluid Power (A Mechanism Adaptable to Pipe Diameters)," *Transactions of the Japan Society of Mechanical Engineers, Part B*, 43(1):29-35 (2000).

\* cited by examiner

$$\tau_{rz} = \tau_y + k \left| \frac{du}{dr} \right|^n \qquad \text{Herschel-Bulkley Constitutive Model}$$

$$r \frac{dp}{dz} = -\frac{\partial (r\tau_{rz})}{\partial r} \qquad \text{Momentum Equation}$$

$$Q = 2\pi \int_{R_p}^{R} ur\,dr + R_p^2 \pi u_p \qquad \text{Volumetric Flow Rate}$$

$$\cdot$$
$$\cdot$$
$$\cdot$$

$$\frac{dp}{dz} = A \frac{4\tau_y}{D} + \left( \frac{3n+1}{n} \frac{8Q}{\pi D^3} \right)^n \frac{4k}{D}; \quad \frac{R_p}{R} \leq 0.5$$

FIG. 8

METHOD AND APPARATUS FOR MEASURING PRESSURE DROP OF MAGNETO-RHEOLOGICAL SUSPENSIONS IN MICROCHANNELS

CROSS REFERENCE TO RELATED APPLICATION

This application claims priority to, and the benefit of, U.S. Provisional Application 60/788,897 filed on Apr. 4, 2006, incorporated herein by reference in its entirety.

STATEMENT OF GOVERNMENT SUPPORT

The work that led to this disclosure was funded in part by EPSCoR grant number 0132556 from the National Science Foundation. The U.S. Government has certain rights in this invention.

FIELD

This disclosure relates to magneto-rheological suspensions such as magneto-rheological fluids and magneto-rheological greases, and more particularly, but not exclusively, to methods for characterizing magneto-rheological suspensions and devices therefore.

BACKGROUND

Magneto-rheological suspensions include dispersions of ferrous and/or ferric particles suspended throughout a carrier matrix. Examples of carrier matrices include hydrocarbon oil, mineral oil, silicon oil, and grease, among others. The particles generally remain suspended throughout the carrier matrix and are often randomly dispersed when the suspension experiences flow. When influenced by a magnetic field, the particles become polarized and are attracted to each other, often forming particle chains that align with the magnetic field. These structures result in an increased apparent viscosity of the suspension that can be proportional to the strength of the applied magnetic field up to a particular strength limit of the applied magnetic field. Above the strength limit, magnetic permeability of the magneto-rheological suspension can become saturated and the apparent viscosity may no longer vary in proportion to the strength of the applied magnetic field.

Demand for miniaturized magneto-rheological devices that utilize magneto-rheological suspensions is increasing. Magneto-rheological suspensions can be used in combination with micro-electro-mechanical systems (MEMS) devices, complex micro-fluid handling systems, control devices for small structures, and cooling devices of macro-scale components. Other examples include small-scale controllable dampers (e.g., shock absorbers) that incorporate microchannels, rotary brakes, and fluid clutches. Alternatively, magneto-rheological suspensions may be used in combination with microvalves, as disclosed in Provisional U.S. Patent Application 60/347,928, filed Oct. 17, 2001, incorporated by reference herein in its entirety, and as disclosed in Provisional U.S. Patent Application 60/334,989, filed Oct. 23, 2001, incorporated by reference herein in its entirety.

Magneto-rheological suspensions can be desirable for use in these devices because magneto-rheological suspensions exhibit variable bulk properties that can be controlled through exposure to electric and/or magnetic fields. For example, magneto-rheological suspensions that exhibit increased apparent viscosity when influenced by a magnetic field can be applied to dampen mechanical energy at variable rates. Future development of miniaturized devices that employ magneto-rheological suspensions requires knowledge of operating characteristics of magneto-rheological suspensions.

SUMMARY

According to one aspect, apparatus are provided for characterizing flow of magneto-rheological materials. An embodiment of the apparatus includes a pump for pumping a magneto-rheological suspension and a microchannel hydraulically coupled to the pump and configured to receive the magneto-rheological suspension from the pump. A manifold is hydraulically coupled between an outlet of the microchannel and the pump. The apparatus also includes a static pressure tap configured to convey a static pressure of the manifold and a pressure sensor hydraulically coupled to the pressure tap and configured to receive the static pressure conveyed therefrom. The apparatus also includes a differential pressure measurement apparatus, wherein a first port of the pressure sensor is hydraulically coupled to the pressure tap. A magnet is positioned to direct a magnetic field toward the microchannel and contents disposed therein. The apparatus in particular embodiments can be used to measure pressure drop across a microchannel through which a magneto-rheological suspension flows.

In some embodiments, the magneto-rheological suspension can include a ferrous and/or ferric alloy particulate suspended throughout a carrier matrix. The carrier matrix can be one or more of a hydrocarbon oil, a mineral oil, a silicon oil, and a grease. Characteristic lengths of the particulate can range from about 0.01 micron to about 50 micron.

The hydraulic diameter of the microchannels can range from about 75 microns to about 750 microns.

In some embodiments, the microchannel can be removably coupled to the pump to be exchangeable for a different microchannel.

The pump can be configured to make adjustable a flow-rate of the magneto-rheological suspension. The pump can include a syringe. The apparatus can further include a tee fitting configured to receive the magneto-rheological suspension. The tee fitting is hydraulically coupled to the syringe to provide means for filling the syringe with the magneto-rheological suspension.

In some embodiments, a second port of the pressure sensor is hydraulically open to atmospheric pressure. In other embodiments, the second port of the pressure sensor can be hydraulically coupled to a second static pressure tap.

The magnet can be or include an electromagnet. The magnetic field can be substantially perpendicular to a longitudinal axis of the microchannel. Further, the magnet can be configured to make adjustable a characteristic strength of the magnetic field.

According to a second aspect, methods are provided for characterizing flow of magneto-rheological materials through a microchannel. An embodiment of the method includes pumping a magneto-rheological suspension at a first flow-rate through a microchannel. A first head-loss is measured across a portion of the microchannel. As the magneto-rheological suspension is pumped at a second flow-rate through the microchannel, a magnetic field is directed toward the microchannel and the magneto-rheological suspension disposed therein. Thus, a second head-loss is measured across the portion of the microchannel.

The method can also include computing a difference between the first head-loss and the second head-loss to determine a measure of the dynamic force response of the magneto-rheological suspension under exposure to the magnetic field. In some embodiments, the first flow-rate and the second flow-rate can be substantially the same.

The method can include deriving a correlation that describes a characteristic of the magneto-rheological suspension relative to a characteristic of the magnetic field and a characteristic of the microchannel. The method can further include expressing the microchannel characteristic according to one or more of a hydraulic diameter, a channel length, a surface roughness, a flow channel arc length, and a flow channel radius of curvature. The method can include expressing the magnetic field characteristic according to one or more of a field strength, a field direction, and a duty cycle of the magnetic field directed toward the microchannel and the suspension disposed therein. Also, the method can include expressing the magneto-rheological suspension characteristic according to one or more of a carrier-medium viscosity, an apparent viscosity, a particle-fill loading, and a filler particle characteristic. The filler-particle characteristic can be expressed according to one or more of a characteristic length, a shape, and a ferrous and/or ferric alloy composition.

The method can also include exchanging the microchannel for a second microchannel and pumping the magneto-rheological suspension at about the first flow-rate through the second microchannel. A first head-loss is measured across a portion of the second microchannel. The magneto-rheological suspension is pumped at about the second flow-rate through the second microchannel and a magnetic field is directed toward the second microchannel and the magneto-rheological suspension disposed therein. Thus, a second head-loss is measured across the portion of the second microchannel.

The foregoing and other objects, features, and advantages will become more apparent from the following detailed description, which proceeds with reference to the accompanying figures.

DETAILED DESCRIPTION

The following describes several embodiments of a method and an apparatus for characterizing flow of magneto-rheological suspensions through microchannels and makes reference to the accompanying drawings that form a part hereof, wherein like numerals designate like parts throughout. The drawings illustrate specific embodiments, but other embodiments may be formed and structural or logical changes may be made without departing from the intended scope of this disclosure. Directions and references (e.g., up, down, top, bottom, left, right, rearward, forward, etc.) may be used to facilitate discussion of the drawings but are not intended to be limiting. Accordingly, the following detailed description shall not to be construed in a limiting sense and the scope of property rights sought shall be defined by the appended claims and their equivalents.

Flow of magneto-rheological suspensions in microchannels is not currently well understood. Some embodiments of magneto-rheological suspensions under influence of a magnetic field tend to flocculate and clog the microchannel. Other embodiments of magneto-rheological suspensions show limited or no response to applied magnetic fields. Such variable response can be influenced by, inter alia, characteristics of the microchannel, characteristics of the magneto-rheological suspension, and characteristics of the applied magnetic field. Accordingly, characterization of the flow behavior of a magneto-rheological suspension in microchannels under various operating parameters is desirable. In particular, head-loss variation according to the particular microchannel, the particular magneto-rheological suspension, and the applied magnetic field parameters is desirable.

Magneto-rheological suspensions under influence of a magnetic field exhibit, in some instances, variable apparent viscosity resulting in part from magnetic attraction between suspended ferrous and/or ferric particles distal from a wall and ferrous and/or ferric particles adjacent a microchannel wall surface. Particles adjacent a wall surface may exhibit a no-slip boundary condition, e.g., particles near the wall may not translate relative to the wall, or such translation may be less than that of particles distal from the wall. Accordingly, friction between near-wall particles and the wall surface, and interaction between particles distal from the wall and near-wall particles influence the apparent viscosity of magneto-rheological suspensions. Further, interaction between particles can be influenced through exposure to a magnetic field. Accordingly, magneto-rheological suspensions exposed to a magnetic field often exhibit increased apparent viscosity. Increased apparent viscosity leads to increased pressure drop through flow channels compared to similar particle laden suspensions not under the influence of a magnetic field. An apparatus and method for characterizing flow of magneto-rheological suspensions through microchannels is thus desirable.

Particular embodiments of magneto-rheological suspensions compatible with this disclosure are described in U.S. Provisional Patent Application 60/895,369, filed Mar. 17, 2007, incorporated herein by reference. In some embodiments, magneto-rheological suspensions include ferrous and/or ferric alloy particulates suspended throughout a carrier matrix such as a hydrocarbon oil, a mineral oil, a silicon oil, and/or a grease. Filler loading, typically characterized by weight percent, can be varied. Characteristic lengths of suspended particulate can range from about 0.01 micron to about 50 micron and can exhibit a variety of shapes. One embodiment of a magneto-rheological suspension includes in excess of ninety percent by weight (90%-wt.) commercially available carbonyl iron micropowder. For example, commercially available HQ grade iron micro-powder, which includes particles of characteristic length ranging from about 0.5 micron to about 2.2 micron in diameter, has been used to form a magneto-rheological suspension.

Figure 1:
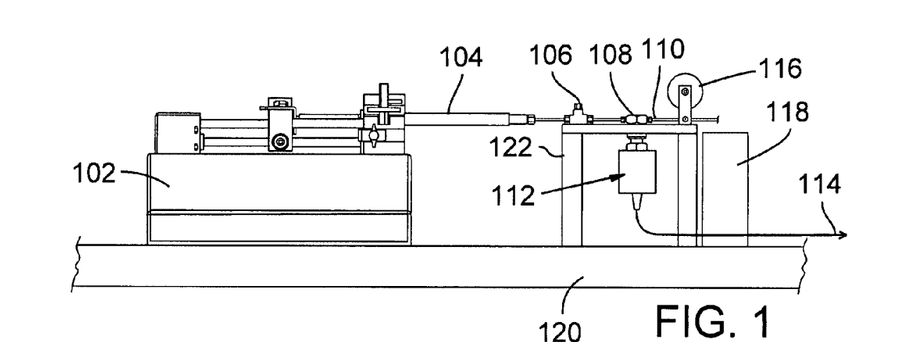
FIG. 1 is a side elevational view of one embodiment of an apparatus for characterizing flow of a magneto-rheological suspension through a microchannel.

FIG. 1 illustrates an embodiment of an apparatus for characterizing flow of a magneto-rheological suspension through a microchannel. The apparatus embodiment can be used to measure pressure drop (head-loss) across a portion of a microchannel 110 through which a magneto-rheological suspension can flow. In embodiments similar to that of FIG. 1, a syringe pump 102 drives a syringe 104 configured to infuse a magneto-rheological suspension into a hydraulic coupling member between a tee fitting 106 and a syringe 104. In some embodiments, the pump 102 can impose a variable flow-rate to the magneto-rheological suspension. Microchannel 110 can be removably coupled to the pump 102 to be exchangeable for a microchannel with different characteristics, for example different geometry or different material. Exemplary embodiments of microchannels have inner diameters ranging from about 75 microns to about 750 microns, such as about 100 microns to about 500 microns. An embodiment similar to that shown in FIG. 1 includes a magnet 116 positioned to direct a magnetic field toward the microchannel 110 and its contents.

The tee fitting 106 can be disposed between a manifold 108 and the syringe 104 to provide means for refilling the syringe 104. The manifold 108 can include a static pressure tap (not shown) configured to convey a static pressure of the manifold 108. Embodiments similar to that illustrated by FIG. 1 include a pressure sensor 112 hydraulically coupled to the pressure tap to receive the static pressure of the manifold 108.

Because the apparatus is intended, in part, to characterize head-loss of a magneto-rheological suspension flowing through a microchannel, the manifold 108 with a static pressure tap desirably is disposed between the pump 102 and the region of the microchannel 110 exposed to a magnetic field. In embodiments similar to FIG. 1, the syringe 104 applies above-ambient pressure to the magneto-rheological suspension upstream of the magnet, resulting in a pressure gradient that drives the magneto-rheological suspension through the microchannel. In other embodiments, the pump 102 draws a vacuum downstream of the magnet 116. In these latter embodiments, the static pressure tap desirably is downstream of the magnet 116. Accordingly, the pressure tap and pressure sensor 112 generally are disposed between the magnet 116 and the pump 102.

Many varieties of pressure sensors are commercially available and usable with the instant embodiments. A typical pressure sensor measures one pressure relative to a reference pressure. For example, a typical pressure sensor that measures a differential pressure includes two ports, a first port configured to be hydraulically coupled to a region with unknown pressure, and a second port configured to be hydraulically coupled to a region of reference pressure. In many embodiments, the second port can be open to atmospheric pressure. In other embodiments, the second port can be hydraulically coupled to a second region of unknown pressure. For example, in an application where head-loss across a hydraulic member is desired, pressure-sensor ports can be hydraulically coupled to each end of the hydraulic member. Examples of differential-pressure sensors include differential-pressure transducers that generate an electrical signal, manometers that generate differences in fluid column height according to differential pressures, and other well-known differential-pressure measurement devices. Some embodiments of the pressure sensor 112 include only a single port. In such embodiments, the reference pressure is often maintained internally to the pressure sensor, for example as a vacuum.

Accordingly, some embodiments employ a first port of the pressure sensor 112 hydraulically coupled to the static pressure tap and a second port that is exposed to atmospheric pressure. In other embodiments, the second port is hydraulically coupled to a region of the microchannel 110 downstream of the magnet 116. In still other embodiments, a port of a second pressure sensor (not illustrated) can be hydraulically coupled to a region of the microchannel 110 downstream of the magnet 116, allowing head-loss to be determined as between the two pressure sensors. In some embodiments, the pressure sensor 112 of FIG. 1 produces an electrical signal in proportion to a pressure differential between the first and second ports. In such an embodiment, the electrical signal can be electrically coupled to a data-acquisition system by a data cable 114. In other embodiments, the pressure sensor may display pressure data using well known analog or digital means.

The apparatus of FIG. 1 can be placed on a bench top 120 and can include support fixtures 122 for the microchannel 110 and pressure sensor 112. A collection container 118 can be positioned under the microchannel exit to capture any ejected magneto-rheological suspension.

In embodiments alternative to that illustrated by FIG. 1, the microchannel 110 can be hydraulically coupled to a collection container 118 by a member (not shown) rather than left open to the atmosphere as illustrated. In some embodiments, the hydraulically coupled collection container 118 can be a second syringe similar to the syringe 104. Some embodiments of the second syringe can be configured to pump a magneto-rheological suspension. Some of the above-described alternatives to FIG. 1 can be configured to pump a magneto-rheological suspension cyclically between the syringe 104 and the second syringe (not illustrated) through the microchannel 110.

In embodiments that incorporate a collection container 118 hydraulically coupled to the microchannel 110, a second static pressure tap that is hydraulically coupled to the microchannel 110 can be disposed between the magnet 116 and the collection container 118. In some embodiments that incorporate a second static pressure tap, first and second ports of a differential pressure sensor 112 can be hydraulically coupled to the static pressure taps and used to determine a head-loss between the static pressure taps. Alternatively, first and second pressure sensors can be hydraulically coupled to the first and second static pressure taps, respectively, and head-loss computed according to a difference between readings of the first and the second pressure sensors.

Figure 2:
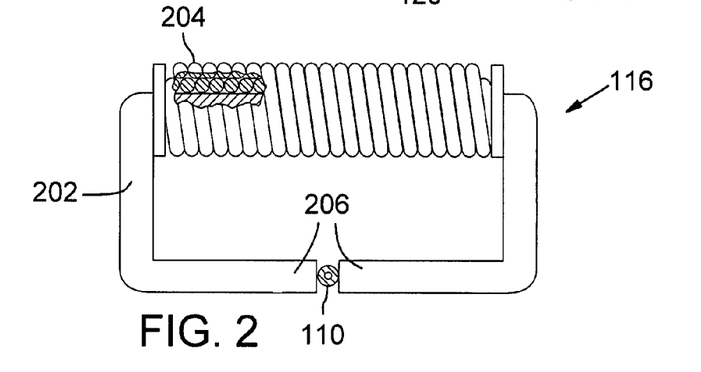
FIG. 2 illustrates a magnet configured to direct a magnetic field toward the microchannel of FIG. 1.

FIG. 2 illustrates an exemplary embodiment of a magnet 116 configured to direct a magnetic field toward the microchannel 110 of FIG. 1. In FIG. 2, the microchannel 110 is disposed between poles 206 of a magnet 116. The magnet 116 can be an electromagnet similar to that shown, a permanent magnet, or a combination thereof. The electromagnet of FIG. 2 includes a core 202 wrapped in part by a coil 204 through which an electric current can pass to induce a magnetic field between poles 206. Coil 204 can have one or a plurality of layers of windings and coil 204 can be wound about a portion of the core 202, or its entirety. Core 202 can have a uniform or variable cross-section throughout its length. In some embodiments, varying the electrical current through the coil 204 will vary a characteristic strength of the magnetic field.

Figure 3A:
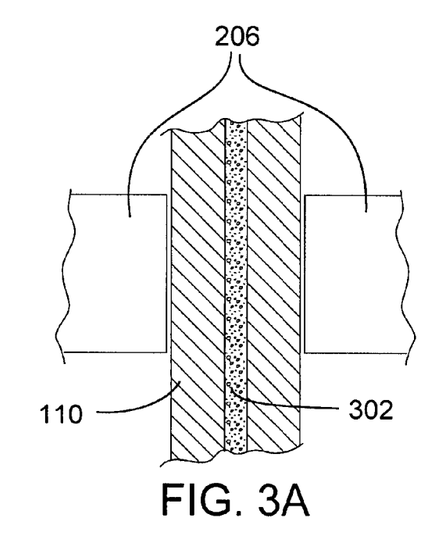
FIG. 3A is an enlarged view of the poles of the magnet in FIG. 2 adjacent to the microchannel of FIG. 2.
Figure 3B:
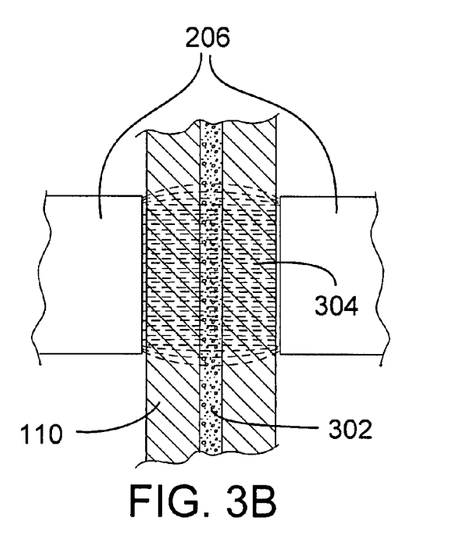
FIG. 3B is an enlarged view of a magnetic field directed toward the microchannel.

The magnetic field 304 acts on the magneto-rheological suspension 302 in the region illustrated by FIGS. 3A-3B. FIG. 3A illustrates an enlarged view of the poles 206 of magnet 116 adjacent to microchannel 110. FIG. 3B illustrates an enlarged view of a magnetic field 304 directed toward microchannel 110 and a magneto-rheological suspension disposed therein. The magnetic field 304 can be substantially perpendicular to a longitudinal axis of the microchannel 110 as illustrated in FIGS. 3A-3B, but other embodiments can direct the magnetic field at other angles.

Figure 4:
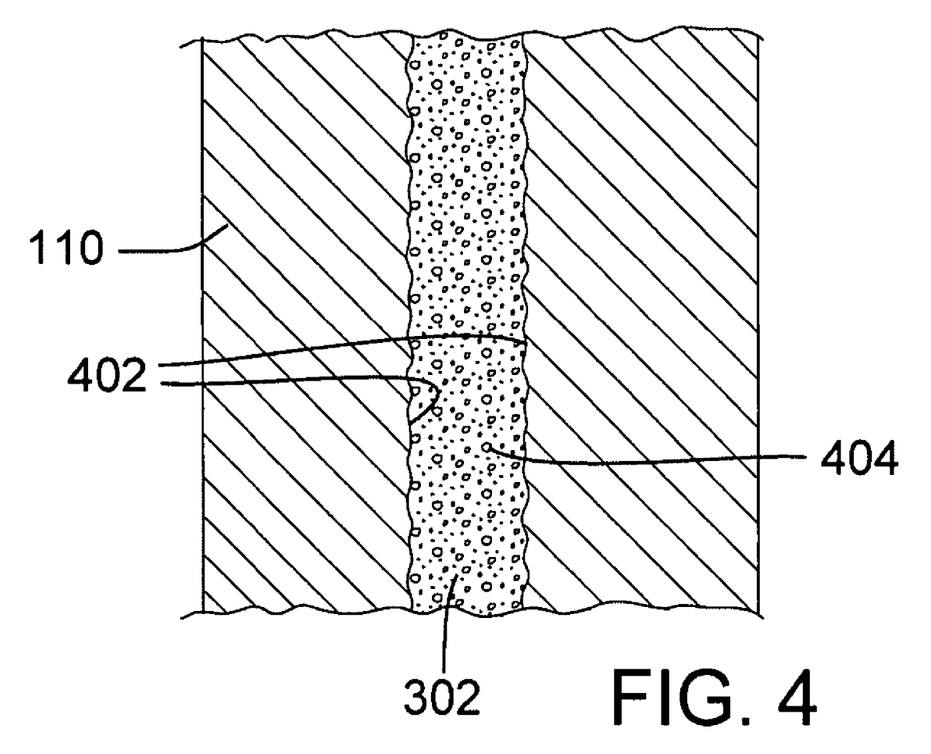
FIG. 4 is a cross-section of a microchannel filled with a magneto-rheological suspension.

Absent a magnetic field 304, as in FIG. 3A, a magneto-rheological suspension 302 can flow through the microchannel 302 impeded by viscous forces primarily associated with particle-laden flows in microchannels. For example, as shown by FIG. 4, an interior surface 402 will often have a roughness that can be of similar magnitude to a characteristic length of a suspended ferrous and/or ferric particle 404. When a magnetic field is present, as in FIG. 3B, a magneto-rheological suspension 302, in particular the suspended ferrous and/or ferric particles 404, tends to form chain or column-like structures aligned with the magnetic field 304 that tend to increase the apparent viscosity of the magneto-rheological suspension. Accordingly, flow resistance (and hence head-loss) tends to increase under influence of a magnetic field 304 compared to flow resistance absent a magnetic field.

Figure 5:
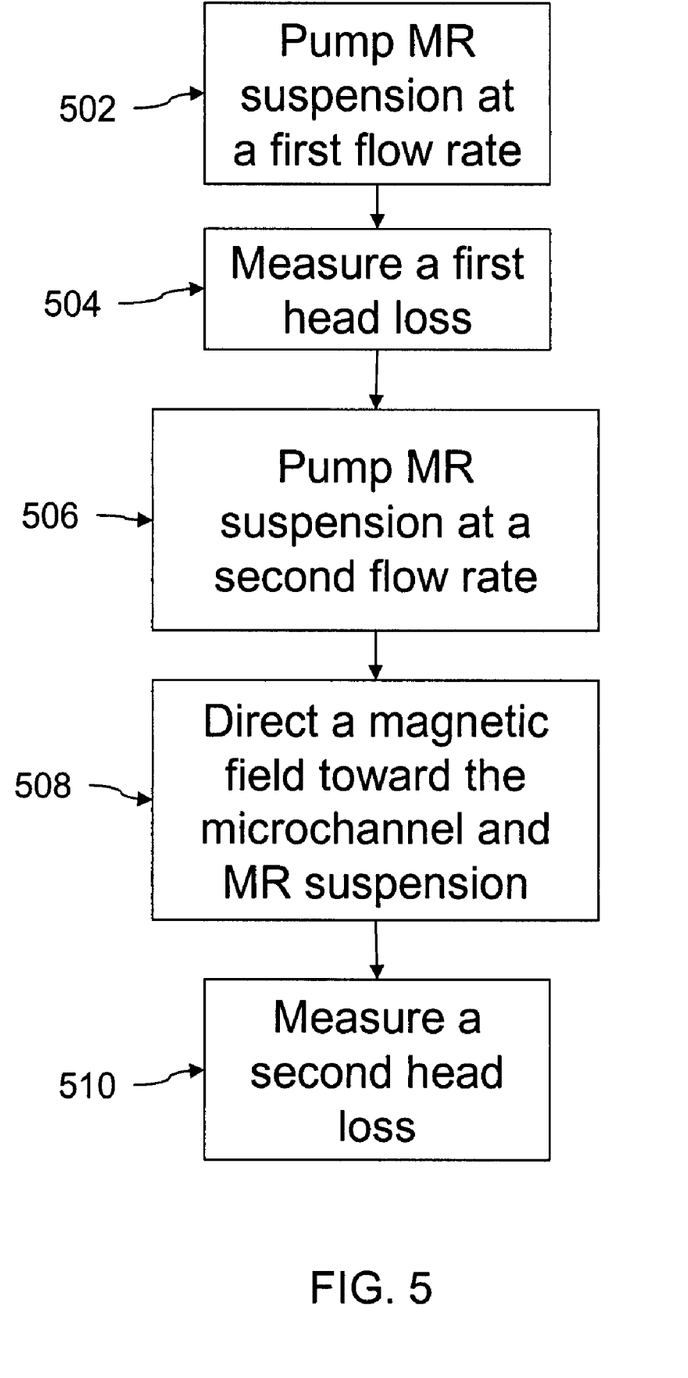
FIG. 5 illustrates a method for characterizing magneto-rheological suspensions.

The apparatus described above can be used to characterize a magneto-rheological suspension, and in particular, head-loss response to various characteristics of the microchannel, the magneto-rheological suspension, and the applied magnetic field. Turning to FIG. 5, one embodiment of a method for characterizing a magneto-rheological suspension is shown. A magneto-rheological suspension is pumped through a microchannel at a first flow-rate at 502. A first head-loss through the microchannel is measured at 504. The suspension is pumped at a second flow-rate at 506 and a magnetic field is directed toward the microchannel and magneto-rheological suspension at 508. In some instances the first flow-rate and the second flow-rate will be substantially the same. A second head-loss through the microchannel is measured at 510.

Methods similar to that shown in FIG. 5 can further include deriving a correlation that describes a characteristic of the flow-field of a magneto-rheological suspension relative to one or more parameters related to the magnetic field, the magneto-rheological suspension, and/or the microchannel. A microchannel can be described according to various parameters, for example, a hydraulic diameter, a channel length, a surface roughness, a flow-channel arc length, or a flow-channel radius of curvature. Similarly, the magnetic field can be described according to various parameters such as field strength, field direction, and even operating duty cycle of the magnetic field. Further, magneto-rheological suspensions can be characterized in a variety of ways that include, but are not limited to, carrier-medium viscosity, apparent viscosity, and particle-fill loading. Filler particles can be characterized according to characteristic length, shape, ferrous and/or ferric alloy composition, and other parameters. Still further, a magneto-rheological flow field can be characterized according to various parameters that include flow-rate, shear stress, and head-loss, among others.

One embodiment of the method shown in FIG. 5 proceeds as follows with regard to the apparatus described above. A syringe 104 configured to withstand high pressures is loaded with a magneto-rheological suspension. The syringe 104 is loaded into a syringe pump 102, or a similar device, for dispensing the magneto-rheological suspension at a controlled first flow-rate. Pressure sensor 112 measures a first pressure upstream of microchannel 110 relative to atmospheric pressure to which the end of the microchannel distal from the pump is exposed. A magnetic field perpendicular to microchannel 110 is directed toward microchannel 110 and the magneto-rheological suspension therein. The pressure sensor 112 measures a second pressure upstream of the microchannel 110 relative to atmospheric pressure.

Figure 6:
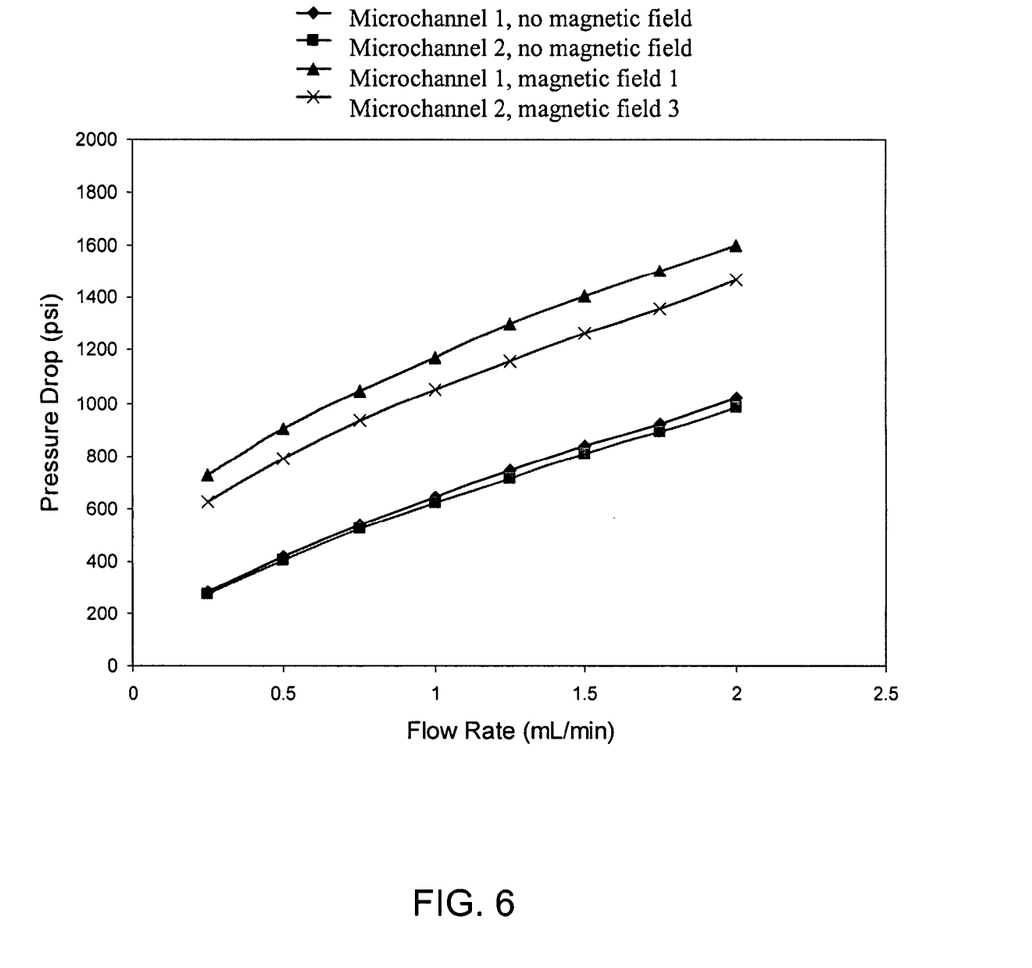
FIG. 6 is a graph of pressure drop variation with flow-rate of a magneto-rheological suspension through different microchannels and exposed magnetic fields of different respective strengths.

Methods as described above can be repeated while varying magneto-rheological-suspension characteristics, microchannel characteristics and magnetic field characteristics to gage, for example, responsiveness of head-loss to each characteristic, as shown by FIG. 6. The exemplary data plotted in FIG. 6 was generated according to two distinct microchannels, each exposed to a similar-strength magnetic field and no magnetic field. As shown by FIG. 6, the tested combinations of microchannel/magneto-rheological suspensions exhibited different head-loss under influence of a magnetic field but similar head-loss in the absence of a magnetic field.

Figure 7:
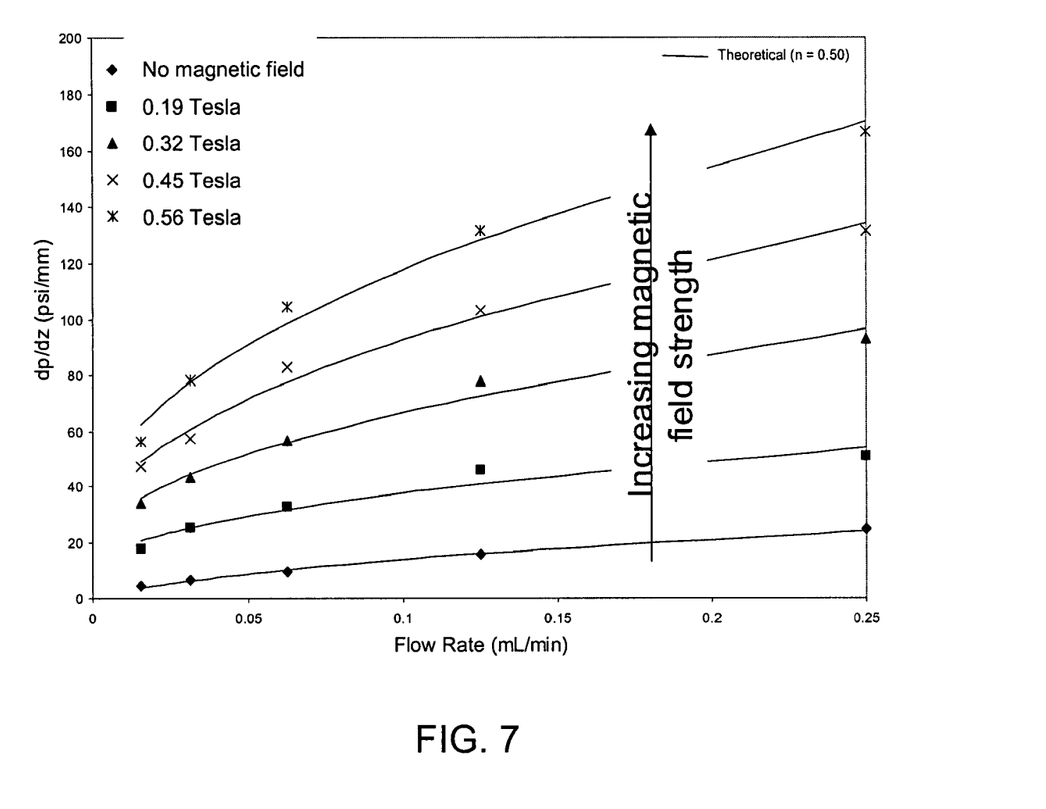
FIG. 7 is graphical comparison of predicted and measured pressure-gradient variations for an exemplary combination of a microchannel and a magneto-rheological suspension under influence of different-strength magnetic fields.
Figure 8:
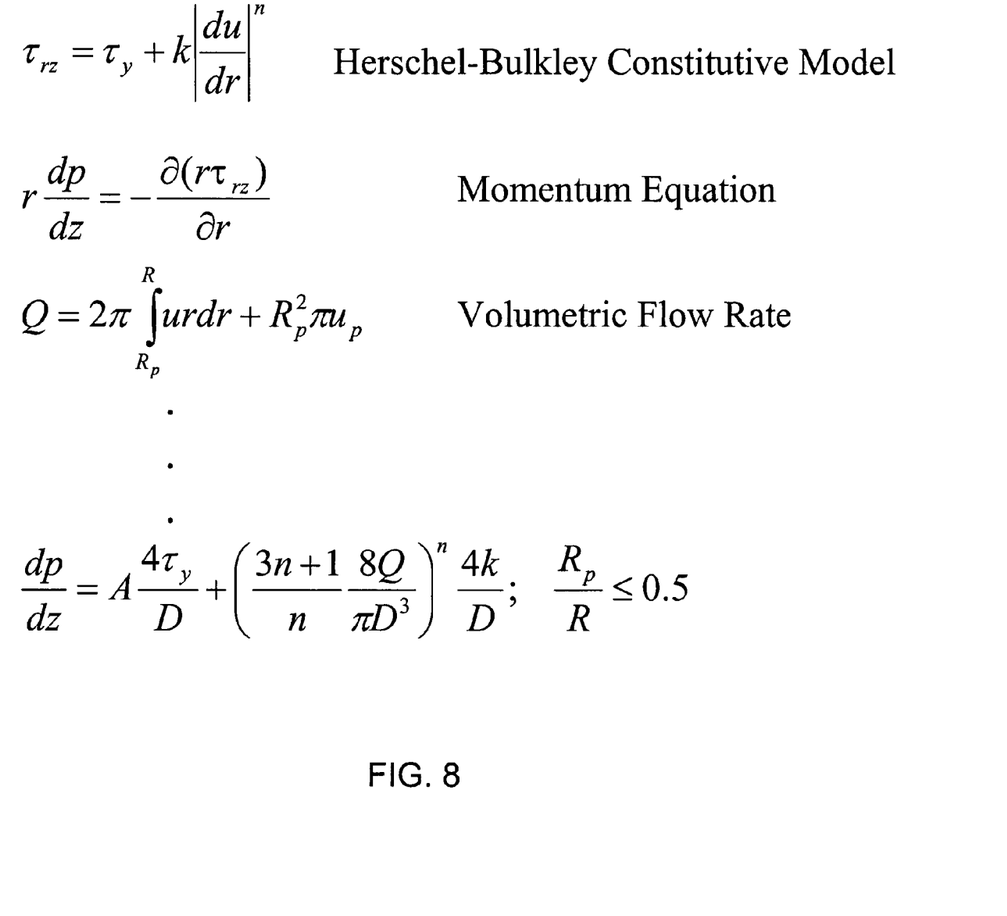
FIG. 8 illustrates exemplary correlations, e.g., constitutive and physical models, for determining pressure-gradient variation (dp/dz) with flow-rate for magneto-rheological suspension flow in a microchannel.

Turning to FIG. 7, predicted and measured pressure-gradient variations (dp/dz) with flow-rate are compared for exemplary combinations of microchannel/magneto-rheological suspensions under the influence of different-strength magnetic fields. Predicted results shown in FIG. 7 were calculated according to exemplary correlations, e.g., constitutive and physical models, as shown in FIG. 8.

In view of the many possible embodiments to which the above disclosed principles may be applied, the illustrated embodiments are only exemplary in nature and should not be taken as limiting. Rather, the scope of protection sought is defined by the following claims. We therefore claim all that comes within the scope and spirit of the following claims.

We claim:

1. An apparatus for characterizing flow of magneto-rheological materials, comprising:
  a pump for pumping a magneto-rheological suspension;
  a microchannel hydraulically coupled to the pump and configured to receive the magneto-rheological suspension from the pump;
  a manifold hydraulically coupled between an outlet of the microchannel and the pump;
  a static pressure tap configured to convey a static pressure of the manifold;
  a pressure sensor hydraulically coupled to the pressure tap and configured to receive the static pressure conveyed therefrom;
  a differential pressure measurement apparatus, wherein a first port of the pressure sensor is hydraulically coupled to the pressure tap; and,
  a magnet positioned to direct a magnetic field toward the microchannel and contents disposed therein.

2. The apparatus of claim 1, wherein the magneto-rheological suspension comprises a ferrous and/or ferric alloy particulate suspended throughout a carrier matrix.

3. The apparatus of claim 2, wherein the caffier matnx comprises one or more of a hydrocarbon oil, a mineral oil, a silicon oil, and a grease.

4. The apparatus of claim 2, wherein a characteristic length of the particulate is about 0.01 micron to about 50 microns.

5. The apparatus of claim 1, wherein a hydraulic diameter of the microchannel is about 75 microns to about 750 microns.

6. The apparatus of claim 1, wherein the microchannel is removably coupled to the pump to be exchangeable for a different microchannel.

7. The apparatus of claim 1, wherein the pump is configured to make adjustable a flow-rate of the magneto-rheological suspension.

8. The apparatus of claim 1, wherein the pump comprises a syringe, the apparatus further comprising a tee fitting configured to receive the magneto-rheological suspension and hydraulically coupled to the syringe to provide means for filling the syringe with the magneto-rheological suspension.

9. The apparatus of claim 1, wherein a second port of the pressure sensor is hydraulically open to atmospheric pressure.

10. The apparatus of claim 1, wherein a second port of the pressure sensor is hydraulically coupled to a second static pressure tap.

11. The apparatus of claim 1, wherein the magnet comprises an electromagnet.

12. The apparatus of claim 1, wherein the magnetic field is substantially perpendicular to a longitudinal axis of the microchannel.

13. The apparatus of claim 1, wherein the magnet is configured to make adjustable a characteristic strength of the magnetic field.

14. The apparatus of claim 1, further comprising:
   a collection container hydraulically coupled to the microchannel; and
   a second static pressure tap hydraulically coupled to a region of the microchannel, wherein the region is disposed between the magnet and the collection container.

15. The apparatus of claim 14, wherein the collection container is configured to pump a magneto-rheological suspension through the microchannel.

16. A method for characterizing a magneto-rheological material, comprising:
   pumping a magneto-rheological suspension at a first flow-rate through a microchannel;
   measuring a first head-loss across a portion of the microchannel;
   pumping the magneto-rheological suspension at a second flow-rate through the microchannel;
   directing a magnetic field toward the microchannel and the magneto-rheological suspension disposed therein; and
   measuring a second head-loss across the portion of the microchannel.

17. The method of claim 16, further comprising computing a difference between the first head-loss and the second head-loss to determine a measure of the dynamic force response of the magneto-rheological suspension under exposure to the magnetic field.

18. The method of claim 16, wherein the first flow-rate and the second flow-rate are substantially the same.

19. The method of claim 16, wherein the magneto-rheological suspension comprises a ferrous and/or ferric alloy particulate suspended in a caffier matrix.

20. The method of claim 19, wherein the carrier matrix comprises one or more of a hydrocarbon oil, a mineral oil, a silicon oil, and a grease.

21. The method of claim 16, wherein the magnetic field is substantially perpendicular to a longitudinal axis of the microchannel.

22. The method of claim 16, further comprising deriving a correlation that describes a characteristic of the magneto-rheological suspension relative to a characteristic of the magnetic field and a characteristic of the microchannel.

23. The method of claim 22, further comprising expressing the microchannel characteristic according to one or more of a hydraulic diameter, a channel length, a surface roughness, a flow-channel arc length, and a flow-channel radius of curvature.

24. The method of claim 22, further comprising expressing the magnetic field characteristic according to one or more of a field strength, a field direction, and a duty cycle of the magnetic field directed toward the microchannel and the suspension disposed therein.

25. The method of claim 22, further comprising:
   expressing the magneto-rheological suspension characteristic according to one or more of a carrier medium viscosity, an apparent viscosity, a particle fill loading, and a filler particle characteristic; and
   if the magneto-rheological suspension characteristic is a filler particle characteristic, expressing the filler particle characteristic according to one or more of a characteristic length, a shape, and a ferrous and/or ferric alloy composition.

26. The method of claim 16, further comprising:
   exchanging the microchannel for a second microchannel;
   pumping a second magneto-rheological suspension through the second microchannel at about the first flow-rate;
   measuring a first head-loss across a portion of the second microchannel;
   pumping the second magneto-rheological suspension through the second microchannel at about the second flow-rate;
   directing a magnetic field toward the second microchannel and the magneto-rheological suspension disposed therein; and
   measuring a second head-loss across the portion of the second microchannel.

27. The method of claim 16, further comprising filling a collection container that is configured to pump a magneto-rheological suspension and is hydraulically coupled to the microchannel, wherein pumping at a second flow-rate results at least in part from the collection container acting on the magneto-rheological suspension.

28. The method of claim 27, wherein:
   pumping at a first flow-rate comprises pumping a magneto-rheological suspension in a first direction relative to a longitudinal axis of the microchannel; and
   pumping at a second flow-rate comprises pumping a magneto-rheological suspension in a second direction opposite the first direction.

* * * * *